United States Patent [19]

Peakman et al.

[11] Patent Number: 5,322,774

[45] Date of Patent: Jun. 21, 1994

[54] PROCARYOTIC LEADER SEQUENCE IN RECOMBINANT BACULOVIRUS EXPRESSION SYSTEM

[75] Inventors: Timothy C. Peakman; Martin J. Page; Ian G. Charles, all of Beckenham, United Kingdom

[73] Assignee: Burroughs Wellcome Co., Research Triangle Park, N.C.

[21] Appl. No.: 780,973

[22] Filed: Oct. 23, 1991

[30] Foreign Application Priority Data

Oct. 24, 1990 [GB] United Kingdom ............... 9023111

[51] Int. Cl.$^5$ ............... C12P 21/06; C12N 7/00; C12N 5/00; C12N 15/00
[52] U.S. Cl. ............... 435/69.1; 435/69.7; 435/235.1; 435/240.2; 435/320.1; 536/22.1; 536/23.1; 536/24.1
[58] Field of Search ............... 435/69.1, 69.7, 320.1, 435/240.2, 235.1; 536/27, 22.1, 23.1, 24.1

[56] References Cited

U.S. PATENT DOCUMENTS 4,879,236 11/1989 Smith et al. ............... 435/235

OTHER PUBLICATIONS

Kozak "Compilation and analysis..." NAR 12:2 1984 pp. 857–872.

Primary Examiner—Robert A. Wax
Assistant Examiner—Hyosuk Kim
Attorney, Agent, or Firm—Nixon & Vanderhye

[57] ABSTRACT

A process for the preparation of a protein, which process comprises culturing under such conditions that the protein is obtained cells infected with a recombinant baculovirus having a promoter, capable of directing the expression of a gene in the cells, operably linked to a heterologous gene which encodes the protein and which is preceded by a leader sequence comprising: T A A T C A T C C A C A G G A G A C T T T C T G [SEQ. ID NO: 1].

20 Claims, 11 Drawing Sheets

Fig. 7a

```
     BamHI "sticky end"                              Translation
                                                       start
  G A T C C T A A T C A T C C A C A G G A C T T C T   A T G
        G A T T A G T A G G T G T C C T G A A G A A   T A C
```

Fig. 7b

```
                          Translation
                            start
  G A T C G C C C G C C A C   A T G
        G C G G G C G G T G   T A C
```

Fig. 9a.

```
          10         20         30         40         50         60
GAATTCATGT TCAGAACCTT TCCTGGCATC CCGAAGTGGA GGAAAACCCA CCTTACATAC
E          N                 B          M
C          L                 S          SF         N
O          A                 T          FO         L
1          3                 1          AK         1
                                        11

70         80         90        100        110        120
AGGATTGTGA ATTATACACC AGATTTGCCA AAAGATGCTG TTGATTCTGC TGTTGAGAAA
                                 S          H                 A
                                 F          I                 L
                                 A          N                 U
                                 1          1                 1

130        140        150        160        170        180
GCTCTGAAAG TCTGGGAAGA GGTGACTCCA CTCACATTCT CCAGGCTGTA TGAAGGAGAG
           M       M MP    HM M                       B          M
           N       B LL    PA L                       S          N
           L       O YE    HE Y                       T          L
           1       2 11    13 1                       1          1

190        200        210        220        230        240
GCTGATATAA TGATCTCTTT TGCAGTTAGA GAACATGGAG ACTTTTACCC TTTTGATGGA
           S                    BN                               A
           A                    SL                               V
           U                    MA                               A
           A                    13                               2

250        260        270        280        290        300
CCTGGAAATG TTTTGGCCCA TGCCTATGCC CCTGGGCCAG GGATTAATGG AGATGCCCAC
B                    S         N          S      E   SH S     AM         S
S                    A         L          E      C   AA E     SS         F
T                    U         A          C      O   UE C     EE         A
1                    6         3          1      1   63 1     11         1

310        320        330        340        350        360
TTTGATGATG ATGAACAATG GACAAAGGAT ACAACAGGGA CCAATTTATT TCTCGTTGCT
                                 NA                  B          F
                                 LV                  B          N
                                 AA                  V          U
                                 42                  1          1

370        380        390        400        410        420
GCTCATGAAA TTGGCCACTC CCTGGGTCTC TTTCACTCAG CCAACACTGA AGCTTTGATG
BN          MH     P  S  S    B            D          H A         R
SL          SA     F  E  E    S            D          I L         S
PA          CE     L  C  C    M            E          N U         A
13          13     1  1  1    1            1          2 3 1       1
```

Fig. 9b.

```
       430        440        450        460        470        480
TACCCACTCT ATCACTGACT CACAGACCTG ACTCGGTTCC GCCTGTCTCA AGATGATATA
                       MP    M        N               B
                       LL    L        L               S
                       YE    Y        A               M
                       11    1        4               1

490        500        510        520        530        540
AATGGCATTC AGTCCCTCTA TGGACCTCCC CCTGACTCCC CTGAGACCCC CCTGGTACCC
    B            M    AD M  MP    M     B     D         S    B  KR    S
    S            N    VR N  LL    L     S     D         E    S  PS    E
    M            L    AD L  YE    Y     M     E         C    T  NA    C
    1            1    21 1  11    1     1     1         1    1  11    1

550        560        570        580        590        600
ACGGAACCTG TCCCTCCAGA ACCTGGGACG CCAGCCAACT GTGATCCTGC TTTGTCCTTT
    N           M  PA    S    B        A          B
    L           N  FL    E    B        L          I
    A           L  LW    C    I        W          N
    4           1  11    1    1        1          1

610        620        630        640        650        660
GATGCTGTCA GCACTCTGAG GGGAGAAATC CTGATCTTTA AAGACAGGCA CTTTTGGCGC
S            M         D              S  DM                      H
F            N         D              A  RS                      I
A            L         E              U  AE                      N
1            1         1              A  11                      1

670        680        690        700        710        720
AAATCCCTCA GGAAGCTTGA ACCTGAATTG CATTTGATCT CTTCATTTTG GCCATCTCTT
    MD         HA                    S    EM           MH           EM
    ND         IL                    A    AB           SA           AB
    LE         NU                    U    RO           CE           RO
    11         31                    A    12           13           12

730        740        750        760        770        780
CCTTCAGGCG TGGATGCCGC ATATGAAGTT ACTAGCAAGG ACCTCGTTTT CATTTTTAAA
      FS      F     N               M        M   PA     M            DM
      OF      N     D               A        A   PV     N            RS
      KA      U     E               E        E   UA     L            AE
      11      1     1               3        1   12     1            11

790        800        810        820        830        840
GGAAATCAAT TCTGGGCCAT CAGAGGAAAT GAGGTACGAG CTGGATACCC AAGAGGCATC
          SHM          M          R      A       M            SF
          AAN          N          S      L       N            FO
          UEL          L          A      U       L            AK
          631          1          1      1       1            11
```

Fig.9c.

```
         850        860        870        880        890        900
    CACACCCTAG GTTTCCCTCC AACCGTGAGG AAAATCGATG CAGCCATTTC TGATAAGGAA
       AM          M      M            CT  S   B
       VA          N      N            LA  F   B
       RE          L      L            AQ  A   V
       21          1      1            11  1   1

910        920        930        940        950        960
    AAGAACAAAA CATATTTCTT TGTAGAGGAC AAATACTGGA GATTTGATGA GAAGAGAAAT
                   M                     B              E       M
                   N                     S              A       B
                   L                     R              R       O
                   1                     1              1       2

970        980        990       1000       1010       1020
    TCCATGGAGC CAGGCTTTCC CAAGCAAATA GCTGAAGACT TTCCAGGGAT TGACTCAAAG
      NN   N   B              A         X          S   MP     M
      CL   L   S              L         M          E   LL     L
      OA   A   T              U         N          C   YE     Y
      13   4   1              1         1          1   11     1

1030       1040       1050       1060       1070       1080
    ATTGATGCTG TTTTTGAAGA ATTTGGGTTC TTTTATTTCT TTACTGGATC TTCACAGTTG
       S          M                             B   AS  M
       F          B                             S   LA  B
       A          O                             R   WU  O
       1          2                             1   1A  2

1090       1100       1110       1120       1130       1140
    GAGTTTGACC CAAATGCAAA GAAAGTGACA CACACTTTGA AGAGTAACAC CTGGCTTAAT
                              M           E    M     M   PA      M
                              A           A    B     A   VL      S
                              E           R    O     E   UU      E
                              3           1    2     3   21      1

1150       1160
    TGTTGATAAC TGCAGGATCC
         P      A    BB
         S      L    AI
         T      W    MN
         1      1    11
```

PROCARYOTIC LEADER SEQUENCE IN RECOMBINANT BACULOVIRUS EXPRESSION SYSTEM

This invention relates to the preparation of proteins by way of a baculovirus expression system.

The baculovirus vector system has been used to express both procaryotic and eucaryotic genes. The expression of these genes is controlled by the polyhedrin promoter of a baculovirus, in particular of *Autographa californica* nuclear polyhedrosis virus (AcNPV). The foreign genes are expressed in insect cells in culture which are infected with recombinant baculovirus incorporating the foreign gene.

In order to obtain a recombinant baculovirus, a baculovirus transfer vector is used. This vector includes the polyhedrin promoter. Baculovirus DNA flanking the polyhedrin gene is provided. The rest of the vector is typically made up of DNA from a bacterial plasmid. A foreign gene is inserted into the transfer vector downstream of the polyhedrin promoter such that its expression is controlled by this promoter.

The transfer vector containing the foreign gene and a baculovirus then co-transfect insect cells susceptible to baculovirus infection. Typically *Spodoptera frugiperda* cell cultures are utilised. Homologous recombination then occurs involving the viral DNA in the transfer vector upstream and downstream of the foreign gene and the corresponding DNA of the baculovirus. The foreign gene and its polyhedrin promoter is therefore transferred to the baculovirus. The recombinant baculovirus is cultured to express the foreign gene.

There are two types of baculovirus transfer vectors. First, there are transfer vectors which include a restriction site into which a foreign gene may be cloned downstream of the polyhedrin ATG start codon for translation. Such transfer vectors result in fusion proteins in which the product of the foreign gene is fused to a N-terminal portion of the polyhedrin peptide.

Second there are transfer vectors which the 5' untranslated leader of the polyhedrin gene ends before the natural ATG translation codon for polyhedrin and a restriction site is then provided. Such a transfer vector is pAc373 in which the 5' untranslated leader ends 8 bases upstream of the natural polyhedrin ATG. Genes cloned into the restriction site are expressed as mature proteins if they contain an ATG followed by an open reading frame coding for the desired product.

In EP-A-0340359 we described and claimed a baculovirus transfer vector which incorporates a restriction site into which a foreign gene may be cloned a short distance downstream of the N-terminus of the polyhedrin gene and in which another triplet of nucleotides is present in place of the natural ATG translation start codon for the polyhedrin gene. A preferred such vector is pAc36C. Increased levels of expression of a protein could be achieved by use of this type of transfer vector.

We have now surprisingly found that expression levels can be further improved by cloning a prokaryotic sequence in front of a heterologous gene it is wished to express. The baculovirus expression system is not a prokaryotic expression system. Rather, expression occurs in insect cells which are classified as higher eukaryotic. Use of the prokaryotic leader sequence of the invention surprisingly results in higher levels of protein expression than if a Kozak sequence is employed instead. A Kozak sequence is a sequence believed optimal for eukaryotic expression.

Accordingly, the present invention provides a process for the preparation of a protein, which process comprises culturing under such conditions that the protein is obtained cells infected with a recombinant baculovirus having a promoter, capable of directing the expression of a gene in the cells, operably linked to a heterologous gene which encodes the protein and which is preceded by a leader sequence comprising:

T A A T C A T C C A C A G G A G A C T T T C T G [SEQ ID NO: 1].

The invention further provides a recombinant baculovirus having a promoter, capable of directing expression of a gene in cells infected with the recombinant baculovirus, operably linked to a heterologous gene which is preceded by a leader sequence comprising:

T A A T C A T C C A C A G G A G A C T T T C T G [SEQ ID NO: 1].

The leader sequence of the invention may be extended at its 5' end, for example by up to 12 or up to 6 further nucleotides. Additional nucleotides may have been provided therefore to enable the leader sequence to be cloned onto a restriction site of a baculovirus transfer vector. The additional nucleotides may therefore represent the sequence of a restriction site or restriction sites. A leader sequence extended at its 5' end to accommodate a Bam HI site is:

A T C C T A A T C A T C C A C A G G A G A C T T T C T G [SEQ ID NO: 2].

This sequence may be provided with a G nucleotide at its 5' end. A sequence incorporating both a Hind III site and a Bam HI site is:

Hind III   Bam HI
A G C T T G G A T C C T A A T C A T C C A C A G G A G A C T T T C T G [SEQ ID NO: 3].

Typically, the leader sequence is fused to the translation initiation codon of the heterologous gene it is wished to express. In such circumstances, therefore, the 3' end of the leader sequence is fused directly to the ATG translation start codon of the heterologous gene. By "heterologous gene" is meant a gene which encodes a polypeptide not ordinarily produced by the cells infected with the recombinant baculovirus. Preferably, the heterologous gene is not a baculovirus gene or an insect cell gene.

The heterologous gene commences with a translation initiation codon. The gene may be a procaryotic or eukaryotic gene. It may be a synthetic gene. The heterologous gene encodes a selected polypeptide. The selected polypeptide may be a physiologically active polypeptide, for example, a polypeptide active in the human body. The polypeptide may be capable of raising antibody. The polypeptide may be tetanus toxin fragment C, stromelysin, pertussis major surface antigen or the HIV integrase protein. Other polypeptides which may be encoded by the heterologous gene include: hepatitis B virus surface antigen; hepatitis B virus core antigen; growth factors such as epidermal growth factor or transforming growth factor; interferons, polypeptides derived from the envelope of an AIDS-associated retrovirus; polypeptides derived from an organism of the genus Plasmodium; polypeptides derived from the Epstein-Barr virus: the heavy chain of a human immunoglobulin molecule; the light chain of a human immunoglobulin molecule; the heavy chain of a mouse immunoglobulin molecule; the light chain of a mouse immunoglobulin molecule; hybrid immunoglobulin molecules e.g. molecules wherein the variable region of the hybrid immunoglobulin molecule is derived from a non-human, such as a mouse, variable region sequence and the constant region of the hybrid immunoglobulin molecule is derived from a human constant region or wherein the complementarily determining regions (CDRs) of the hybrid immunoglobulin molecule are derived from a non-human immunoglobulin such as a murine immunoglobulin and the remaining sequences of the hybrid immunoblogulin molecule are derived for a human immunoglobulin; and fusion polypeptides which comprise a hybrid immunoglobulin molecule contiguous with or connected through an amino acid sequence to an enzyme molecule.

The promoter is typically the polyhedrin promoter. The baculovirus is preferably *Autographa californica*. The cells which are infected with the recombinant baculovirus are generally cells of a cell line of insect cells. Cells of *Trichoplusia ni, Spodoptera frugiperda, Heliothis zea* or *Manduca sexta* may be used. The cells are preferably cells of a *Spodoptera frugiperda* cell line.

The cells which are infected with the recombinant baculovirus are typically cultured according to standard procedures (Summers, M. D. and Smith, G. E., 1987. A manual of methods for baculovirus vectors and insect cell culture procedures, Texas Agricultural Experimental Station, Bulletin No. 1555). The desired protein is expressed. It may then be isolated and purified.

The recombinant baculovirus may be prepared by a process comprising:

(a) providing a recombinant baculovirus transfer vector having a promoter, capable of directing expression of a gene in cells infected with the recombinant baculovirus, operably linked to a heterologous gene which is preceded by a leader sequence comprising: T A A T C A T C C A C A G G A G A C T T T C T G [SEQ ID NO: 1].

(b) co-transfecting cells susceptible to baculovirus infection with the recombinant baculovirus transfer vector and with intact wild type baculovirus DNA.

The cells which are transfected in step (b) are generally cells of a cell line of insect cells. Cells of *Trichoplusia ni, Spodoptera frugiperda, Heliothis zea* or *Manduca sexta* may be transfected. Preferably the cells are cells of a *Spodoptera frugiperda* cell line. The recombinant baculovirus transfer vector typically comprises DNA from the baculovirus *Autographa californica* flanking the promoter, leader sequence and foreign gene. The wild-type baculovirus DNA which also transfects the cells is then the genomic DNA of *Autographa californica*.

Following homologous recombination, the promoter, leader sequence, foreign gene and flanking viral DNA from the recombinant transfer vector are transferred to the wild-type baculovirus DNA. Recombinant baculovirus is screened for, for example by plaque assay. The recombinant baculovirus can be purified.

The recombinant baculovirus transfer vector which is employed in step (a) also forms part of the invention. Such a transfer vector may be prepared by cloning a DNA sequence consisting essentially of the heterologous gene and the leader sequence of the invention into a baculovirus transfer vector. The DNA sequence is cloned into the transfer vector at an appropriate restriction site so that it is under transcriptional control of the promoter that will direct expression of the gene. The transfer vector is preferably pAc36C, in which case the DNA sequence is cloned into the Bam HI site in the vector.

Alternatively, the recombinant baculovirus transfer vector may be prepared from a transfer vector which incorporates the leader sequence. A heterologous gene may be cloned into the transfer vector at a restriction site immediately downstream of the leader sequence. A preferred transfer vector of this type comprises:

(i) a restriction site into which a foreign gene may be cloned downstream of the N-terminus of the polyhedrin gene, (ii) another triplet of nucleotides in place of the natural ATG translation start codon of the polyhedrin gene, (iii) from up to the first 24 to up to the first 50 bases of the polyhedrin gene, and (iv) the leader sequence of the invention downstream of (iii) but prior to (i).

Preferably from up to the first 27 to up to the first 39 bases of the polyhedrin gene are present. Up to the first 33 bases may be present. These bases may be followed by a linker sequence of up to 10 bases, for example of up to 5 bases, before the leader sequence. Alternatively, no linker sequence may be present. The leader sequence is typically immediately followed by the restriction site (i).

The DNA sequence comprising the leader sequence and a heterologous gene is typically prepared by constructing the leader sequence and fusing the leader sequence to the gene. A heterologous gene sequence for use in the invention may be prepared by synthesis, for example by annealing overlapping oligonucleotides. Alternatively, it may be a cloned or a cDNA sequence.

The following Examples illustrate the invention.

BRIEF DESCRIPTION OF THE DRAWINGS

FIG. 7 shows the sequences of the nucleotides used in the construction of pAc36CHIVK and pAc36CHIVP;

FIGS. 9a, 9b and 9c are restriction maps of the 1.2 kb EcoRI-BamHi fragment employed in Example 2, in which the translation start codon is underlined.

EXAMPLE 1

Expression of Tetanus Toxin Fragment C

1. Materials and Methods

Bacterial strains and recombinant DNA techniques

E. coli strain TG1 and plasmid pTETtac2 have been described previously (Makoff et al, Biotechnology 7, 1989, 1043-1046; WO 90/15871). DNA manipulations were performed as described by Maniatis et al ("Molecular Cloning: A Laboratory Manual, Cold Spring Harbor Lab., Cold Spring Harbor, N.Y., US, 1982).

Baculovirus procedures

Baculovirus recombinants were generated by cotransfection of 1 μg AcNPV DNA with 2 μg recombinant plasmid DNA (prepared by the method of Birnboim and Doly, Nucl. Acids Res 7, 1979, 1513) into Spodoptera frugiperda cells by calcium phosphate precipitation. After 4 hours, the cells were rinsed once, re-fed with TC100 medium (FLow Labs) and cultured for 3 days at 28° C. Supernatants were then plaque titrated and screened visually for inclusion negative plaques. Stocks of S. frugiperda cells were maintained in spinner flasks (Techne) at room temperature. Plaque assays were performed by seeding S. frugiperda cells into 35 mm petri dishes at $10^6$ cells/dish, adhering for 10-15 minutes at room temperature, and then infecting with 100 μg virus/dish. After one hour at room temperature virus inoculum was removed by aspiration and monolayers overlayed with 1% agarose (2 volumes TC100 plus 1 volume 3% Seaplaque LGT agarose). When set, a further 1 ml of TC100 was overlaid on the agarose. After 3 days at 28° C. the TC100 was removed and plaques visualised by staining for 1 hour with 1 ml/dish of 10% neutral red (BDH) in PBS. Plaque purified clones were expanded in Techne spinner flasks at 28° C.

Immunisation procedures

Mice were immunised with recombinant fragment C in alhydrogel and were tested for immunity to tetanus by toxin challenge as described previously (Fairweather et al. Infect. Immun. 55, 1987, 2541-2545).

Affinity chromatography and ELISA

Fragment C was purified from S. frugiperda extracts by affinity chromatography using monoclonal antibody TT08 (Sheppard et al, Infect. Immun. 43, 710-714, 1984) bound to cyanogen bromide activated Sepharose (Trade Mark) 4B. Fragment C was eluted with 0.1M sodium citrate pH 3.0 and was neutralised by the addition of an equal volume of 0.1M sodium phosphate. Fragment C was assayed by an enzyme-linked immunosorbent assay (ELISA) as described previously (Makoff et al, 1989).

2. Results and Discussion

Cloning of fragment C into baculovirus

The structural gene for fragment C is present on pTETtac2, an E. coli expression plasmid which directs the synthesis of fragment C at 3-4% total cell protein (Makoff et al, 1989). As fragment C is a cleavage product of tetanus toxin, pTETtac2 directs the synthesis of mature fragment C- with a methionine residue at the N-terminus. A 1.4 BglII-BamHI fragment, containing the entire fragment C structural gene was preceded by the sequence AGATCTTAATCATCCACAGGAGACTTTCTGATG [SEQ ID NO: 4], was cloned into the unique BamHI site of p36C which is a high level baculovirus expression vector (Page, Nucl. Acids Res. 17, 454, 1989).

Figure 1:
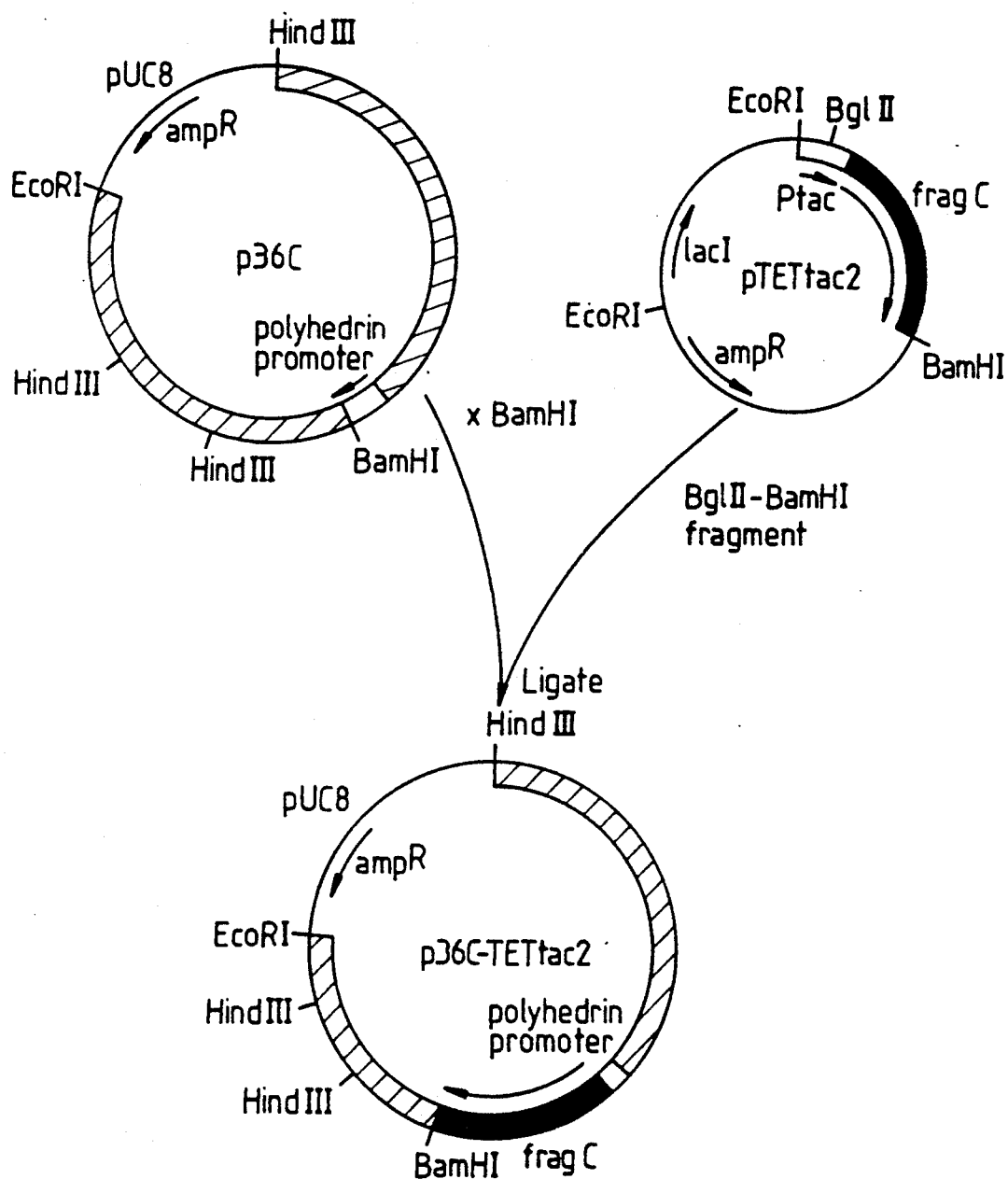
FIG. 1 shows the construction of p36C-TETtac2.

The resulting plasmid, p36C-TeTtac2 (see FIG. 1) was cotransfected with baculovirus AcNPV DNA into S. frugiperda cells by calcium phosphate precipitation. Cells containing recombinant viruses were identified by screening for inclusion negative plaques, and after plaque purification several recombinants were screened for the production of fragment C by SDS-PAGE and Western blotting (data not shown).

One recombinant, BVFC1, was studied further. S. frugiperda cells were infected with BVFC1 at a multiplicity of infection of 0.1. Cells were taken at daily intervals for analysis by sodium dodecyl sulphate-polyacrylamide gel electrophoresis (SDS-PAGE). Fragment C was synthesised by BVFC1 infected cells at days 2-4, with the maximum amount being produced on day 3. Fragment C was clearly one of the major polypeptides produced by the cells, at a level only slightly lower than polyhedrin.

S. frugiperda cells were grown in spinner flask culture and were infected with BVFC1 virus at an m.o.i. of 10. After 4 days, cells were harvested, lysed by sonication and a soluble extract was obtained by low and high speed centrifugation. The cell proteins were then analysed by SDS-PAGE and Western blotting. A band of 50 kD was one of the major proteins in the cell extract. Its identity as fragment C was confirmed by Western blotting against anti-fragment C sera.

Very high expression of fragment C was thus obtained (about 400 μg/ml). The fragment C was purified from the cell extract by affinity chromatography using monoclonal antibody TT08. Fragment C purified in this was judged to be 80% pure as determined by SDS-PAGE.

Immunogenicity of fragment C expressed by baculovirus

Fragment C from C. tetani or E. coli is able to protect mice from challenge with tetanus toxin. In order to determine whether fragment C produced from baculovirus retained this activity, mice were immunised with the soluble extract of S. frugiperda cells which had been infected with baculovirus BVFC1. Preliminary results indicated that such preparations had immunising activity (data not shown). This test was repeated with immunopurified fragment C followed by challenge with tetanus toxin. The results are shown in Table 1.

TABLE 1

Immunisation of mice with recombinant fragment C expressed from Baculovirus

| Treatment | Amount (μg)[a] | Survivors[b] One dose | Two doses |
|---|---|---|---|
| Frag C | 1 | 10 | 10 |
| Frag C | 0.25 | 10 | 10 |
| Frag C | 0.06 | 0 | 10 |
| Frag C | 0.01 | 0 | 0 |
| PBS |  | 0 | 0 |
| Frag C[c] |  | 10 | 10 |

[a]Antigen in alhydrogel was injected into BALB/c mice subcutaneously. The second dose as given 4 weeks after the primary injection.
[b]Mice (n = 10 per group) were challenged with 50 LD$_{50}$s of tetanus toxin 4 weeks after the last injection.
[c]Derived from tetanus toxin.

Mice immunised with one dose of 0.25 μg or with two doses of 0.06 μg were fully protected against tetanus challenge, indicating that the fragment C expressed by baculovirus was biologically active in this assay. The levels of fragment C necessary for immunity are similar to those required of fragment C derived from *C. tetani* or *E. coli* (Makoff et al, 1989) showing comparable activity of the baculovirus expressed material.

EXAMPLE 2

Expression of the Stromelysin Protein

1. General

Expression of fragment C in Example 1 had not been compared with expression of fragment C using a sequence believed optional for eukaryotic translation (a Kozak sequence). The baculovirus expression system, in which expression occurs in insect cells, is classed as higher eukaryotic. The translation rules would be expected to conform to the Kozak rules determined for mammalian genes, although there is no experimental evidence that Kozak rules apply. The leader of the invention employed in Example 1 is very sub-optimal with respect to the concensus Kozak sequence, though.

Experiments were therefore conducted to compare the leader sequence of the invention with Kozak sub-optimal, Kozak optimal and Kozak perfect sequences. The first set of experiments involved expression of the stromelysin protein. Two constructs were made and assayed. The first construct was a recombinant baculovirus termed v36ST1 which was sub-optimal around the translation initiation codon ATG for the Kozak consensus sequence:

v36ST1 5' GATCCGAATTC ATG T 3'[SEQ ID NO: 5]

The second construct was a recombinant baculovirus termed v36STM2 which contained the leader sequence of the invention fused to the translation initiation codon of the stromelysin gene. The infected cells were assayed by determining protease activity. The protease activity of cells infected with v36ST1 was indistinguishable from background activity (about 400 units). The activity of uninfected cells and cells infected with wild-type virus was similarly low (200-300 units). In contrast, cells infected with v36STM2 had a protease activity of about 8000 units, i.e. a stimulation of 20-fold. In more detail:

2. Construction of transfer vectors p36CST1 and p36CSTM2

The transfer vectors, p36CST1 and p36CSTM2, containing the engineered stromelysin gene were derived from pAc36C (Page, 1989). The entire stromelysin gene (Whitham et al, Biochem. J. 240, 913-916, 1986; EMBL database, code HSSTROMR) was synthesised as a 1.2 kb EcoR1-BamHI fragment (FIG. 9), which was cloned into the pUC18 plasmid. This fragment was purified by gel electrophoresis and electroelution, ligated to one or other of the two oligonucleotides shown in FIG. 2a and then cloned into the BamH1 site of Bluescript KS. The resulting plasmids were designated pKSST1 (FIG. 2a(i)) and pKSST2 (FIG. 2a(ii)).

Figure 3:
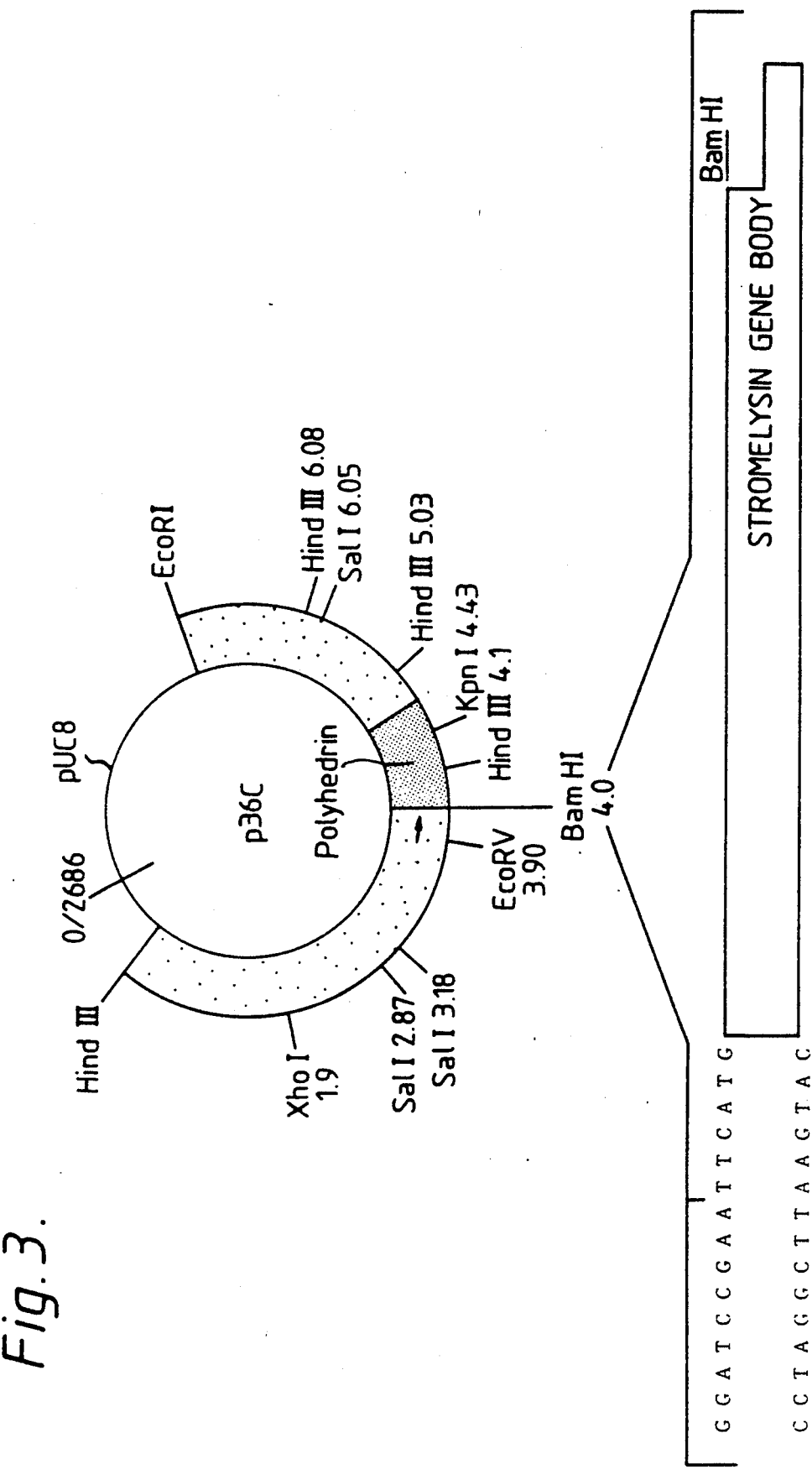
FIG. 3 shows the structure of p36CST1.

Plasmid pKSST1 was digested with BamH1 and the 1.2 kb fragment purified by gel electrophoresis followed by gel electroelution and cloned in the correct orientation into the baculovirus transfer vector pAc36C. This plasmid was called p36CST1 (FIG. 3). 3. Construction of p36CSTM2—mutagenesis of pM13ST2

Figure 2:
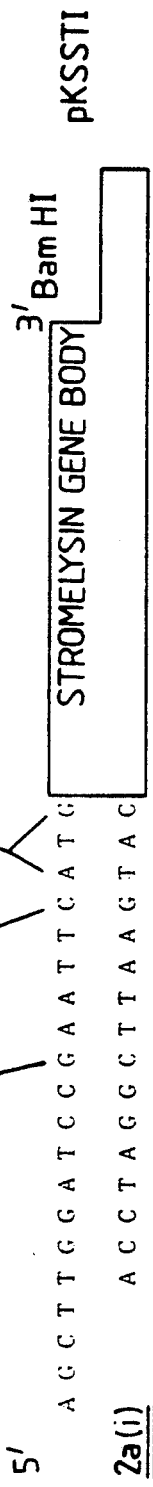
FIG. 2 shows (a) the construction of transfer vectors p36CST1 and p36CSTM2 and (b) the oligonucleotide used for oligonucleotide directed mutagenesis on the M13 derivative of pKSST2.
Figure 2:
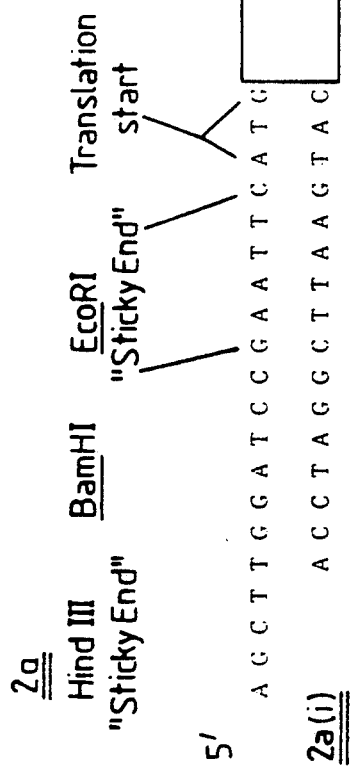
Figure 2:
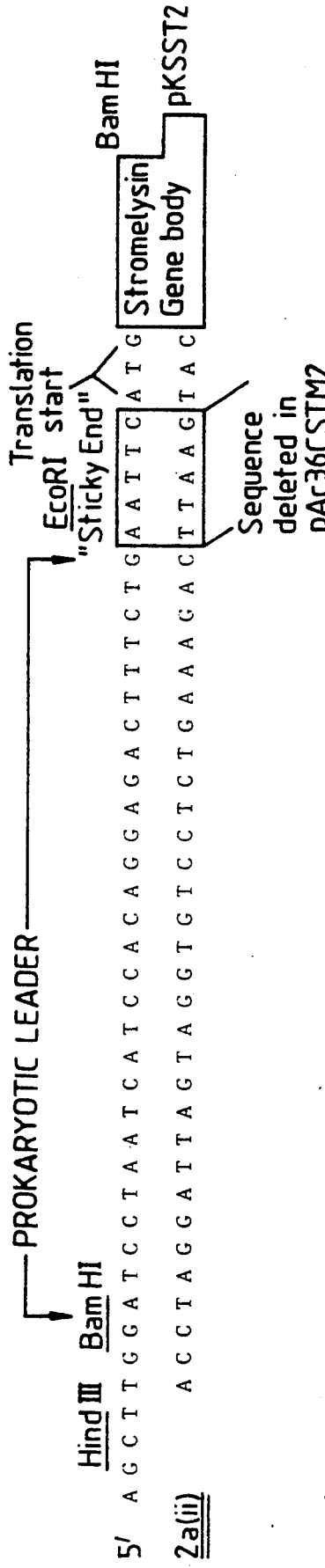

The 1.2 kb BamH1 fragment from pKSST2 was purified by gel electrophoresis followed by gel electroelution and cloned into the BamH1 site of the replicative form in the antisense orientation of the M13 mp19. This plasmid was called pM13ST2. However, in order to regenerate exactly the sequence of the prokaryotic leader it was necessary to delete the sequence AATTC positioned before the translation initiation codon of the stromelysin gene. This was done using the Amersham International oligonucleotide mutagenesis kit, and single strand M13 template derived from pM13ST2. The oligonucleotide used is shown in FIG. 2b. The sequence position around the translation start of the mutated form, pM13STM2, was confirmed by DNA sequencing. The 1.2 kg BamH1 fragment from pM13ST2M was purified from the replicative form of the plasmid and cloned in the correct orientation into the baculovirus transfer vector pAc36C. The resulting plasmid was called pAc36CSTM2.

4. Generation of recombinant virus

*Spodoptera frugiperda* (Sf21) cells (Vaughen et al, In vitro, 13 213-217, 1977) were grown in suspension cultures at 27° C. in TC100 medium (Flow Laboratories), supplemented with 10% foetal bovine serum (Gibco) and 5 $\mu$g/ml gentamycin. AcNPV was propagated in Sf21 cells grown at 27° C. in suspension cultures. Recombinant viruses containing the heterologous gene sequences were generated by co-transfection of a 20:1 molar ratio of the recombinant transfer vectors p36CST1 and p36CSTM2 with AcNPV DNA purified from extracellular virus (ECV) cultures in Sf21 cells. The method of purification of AcNPV DNA was as described (Summers and Smith, 1987, "A Manual of methods for Baculovirus vectors and Insect cell culture procedure"), except that cultures were infected at 0.1 pfu per cell and harvested after 6 days and the sucrose gradient step was omitted. Co-transfection was as described (Summers and Smith 1987, Method 1).

The resultant ECV was screened for recombinants by standard agarose overlay plaque assay (Brown and Faulkner, 1977, J. Gen. Virol, 36, 361-364) using serial dilutions of the transfection culture supernatant. Following neutral red staining, potential recombinant plaques were selected visually by screening for the absence of polyhedra, picked into 0.5 ml of culture medium and purified by repeated plaque assay. Recombinant viruses were scaled up to high titre (>$10^8$ pfu/ml) by infection of monolayer cultures of Sf21 cells at 27° C. The resulting high titre viruses were called v36CST1 and v36CSTM2.

5. Analysis of proteins from cells infected with the recombinant viruses

The structure of the recombinant viruses described in section 4 was confirmed by Southern blotting. Polyhedrin negative, insert positive plaques were picked into 0.5 mls of culture medium and allowed to diffuse for at least 1 hr. A 100 $\mu$l aliquot of this was used to infect $2 \times 10^6$ Sf21 cells in a 35 mm tissue culture dish, which was incubated at 27° C. for 1 hr. The inoculum was removed and replaced with 1 ml of fresh culture medium and the plates incubated at 27° C. for three days. The cells were then washed in phosphate buffered saline solution (PBS) and removed.

6. Protease activity of baculovirus expressed stromelysin

Figure 4:
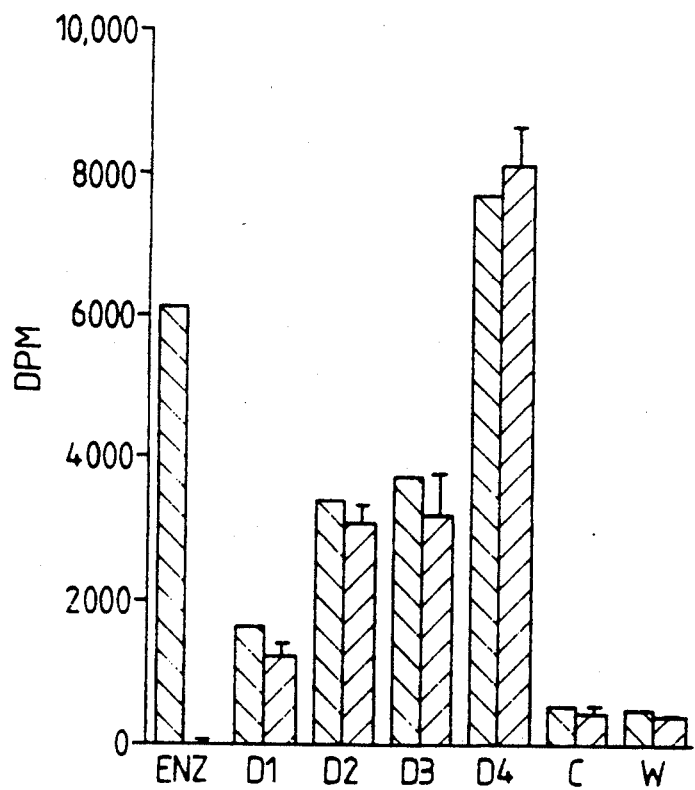
FIG. 4 shows the activity of cell lysates infected with v36CSTM2 on days 1, 2, 3 and 4 post-infection in the presence (□) or absence (□) of tissue metalloproteinase inhibitor (TIMP), C denoting control, W denoting wild-type baculovirus, DPM denoting disintegrations per minute and ENZ denoting a control aliquot of pure enzyme.

The proteins expressed from the recombinant viruses were assayed as follows. Infected cells were lysed with 1% Nonidet P40(NP40) and 150 mM NaCl and the membranous material was removed by centrifugation. The remaining lysate was incubated with tritiated casein (200 $\mu$g in 100 $\mu$l Tris buffer—Sigma), The reaction was incubated at 37° C. for 2 hours and terminated by the addition of 50 μl of a 30% of trichloroacetic acid (TCA). The activity of the stromelysin was determined by measuring the TCA precipitated radioactivity. FIG. 4 shows the results of this assay on v36STM2. The values obtained for v36ST1 were virtually indistinguishable from background and are not included.

Surprisingly, presence of tissue metalloproteinase inhibitor (TIMP), an inhibitor of stromelysin, did not reduce the activity observed in the cell lysates. It is proposed that a factor in the lysate inhibits the action of stromelysin. Evidence to support this comes from the observation that if the lysates from the negative controls are "spiked" with a known amount of pure active stromelysin, then the observed activity is lower than that expected.

EXAMPLE 3

Expression of Pertussis Major Surface Antigen

1. General

Two constructions were initially expressed in baculovirus. The first, called vP60pl, encoded the pertussis major surface antigen (molecular weight=60 kDa) and was expressed in p36C and contained the leader of the present invention. Expression of this protein in insect cells infected with vP60pl was very efficient (400–500 μg/ml). The second construction, vP40, was a truncated form of the major surface antigen. The sequences upstream of this gene were Kozak optimal, though not Kozak perfect, as follows:

```
                                        [SEQ ID NO: 6]
vP40                      G A A T T C A A T A T G G
Kozak Concensus (C C C) (G C C) G C C  A C C A T G G
                                *      * * * *
                                       Translation
                                       initiation
                                       codon
```

Those bases starred (*) in the Kozak concensus are more important in translation. Those in brackets are less important. Expression of the 40 kDa protein in cells infected with vP40 was still efficient (about 100 μg/ml) but 4–5 fold lower than expression of P60 from vP60pl infected cells.

The experiment that was then done was to make a recombinant virus expressing the 40 kDa protein preceded by the same prokaryotic leader as in vP60pl. Expression of the 60 kDa protein and the 40 kDa protein from the two constructions was determined. Expression of the 40 kDa protein was 3–4 fold higher from vP40pl than from vP40 and approached the levels of protein expressed from vP60pl.

2. Construction of p36CP60pl, p36cP40 and p36CP40pl

Figure 5:
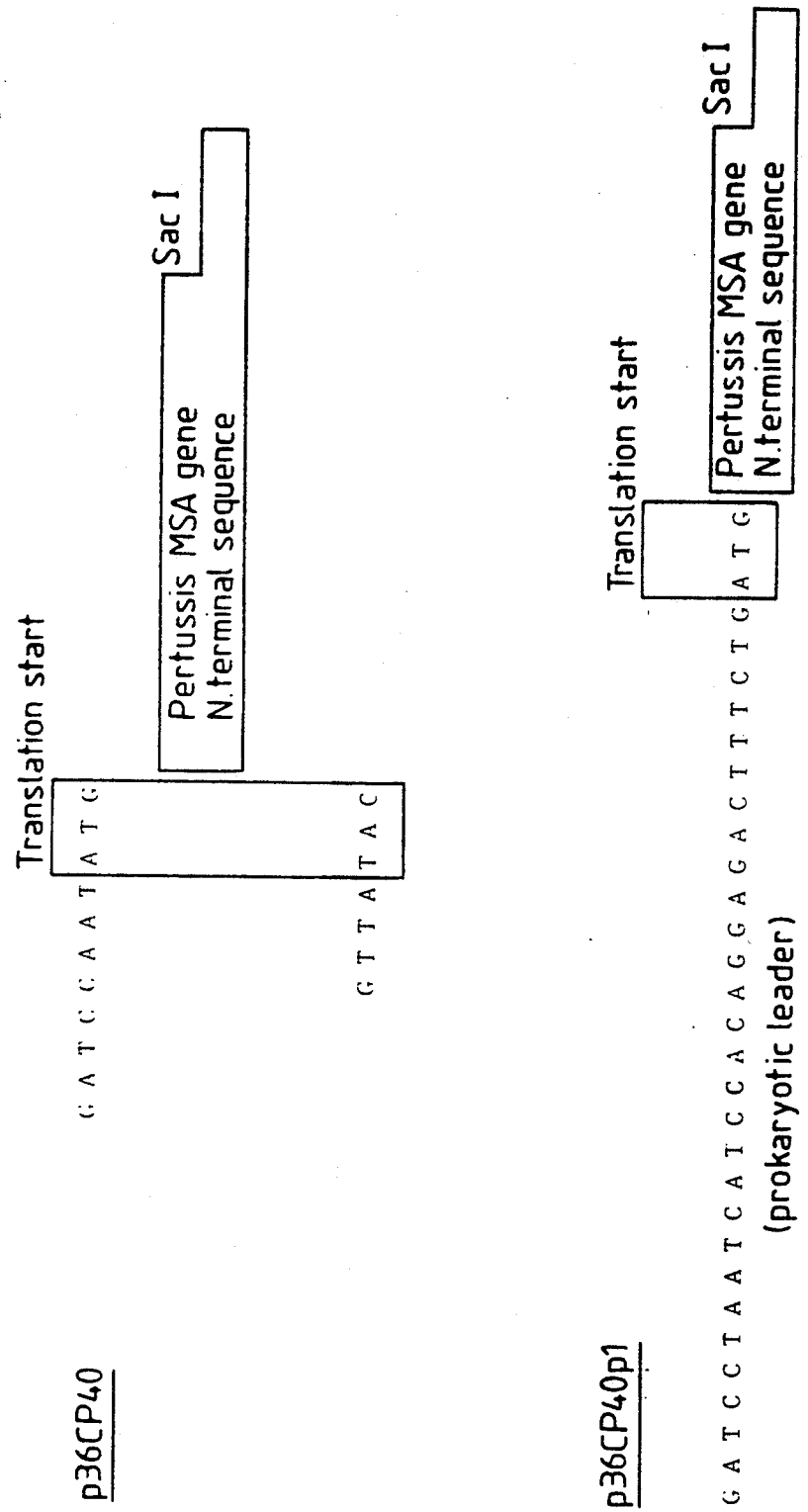
FIG. 5 shows the sequences of the oligonucleotides used in the construction of p36CP40 and p36CP40pl.

The plasmids p36CP40 and p36CP40pl were made by fusing the pertussis major surface antigen (PMSA) gene body lacking its N-terminus to synthetic oligonucleotides containing various translation leaders and the N-terminus of the PMSA. The sequence of oligonucleotides used in the construction of the two plasmids is shown in FIG. 5.

(i) Construction of o36CP60pl

The 1.8 kb BglII-BamHI fragment from pPertac 7, containing the PMSA coding sequence fused to the leader of the invention, was purified by gel electrophoresis and gel electroelution and cloned into the Bam H1 site of the baculovirus transfer vector pAc36C (Page, 1989). The resulting plasmid was called p36CP60pl.

(ii) Construction of pAc36CP40 and pAc36CP40pl

The 4.6 kbp Bgl II - Sac I fragment from pPertac 9 (derived from pPertac 7, Makoff et al.) was purified by electrophoresis followed by electroelution. An oligonucleotide pair containing a Kozak optimal sequence was cloned into this vector as a Bgl II-SacI fragment. After sequencing, the 1.1 kbp Bgl II - Bam H1 fragment was cloned in the correct orientation into the Bam HI site of pAc36C. The resulting plasmid was called pAc36CP40.

Plasmid pAc36CP40pl was constructed in two stages. The 1.1 kbp Bgl II - Bam H1 fragment of pPertac 7 (Makoff et al, Biotechnology 8, 1990, 1030–1033) was purified and cloned into the Bam H1 site of pUC9 in the antisense orientation. This plasmid was called pUC69-6. A pair of oligonucleotides, containing the leader of the invention and the N-terminal sequence of the 40 kDa protein, was cloned as a Bam H1 - Hind III fragment into the replication form of M13 mp19. The sequence of the oligonucleotide was confirmed by DNA sequencing. The Bam Hl-Hind III insert from the replicative form of this construction was purified and cloned between the Bam HI and Hind III sites of the pUC9 plasmid. The resulting plasmid was designated pUC9-3.

The pUC9-3 plasmid was digested with Sac I and Hind III and the 3.0 kb fragment, containing the leader of the invention, the N-terminal sequence of the 40 kDa protein and the pUC9 vector body, was isolated. The 1.1 kbp Sac I - Hind III fragment, containing the C-terminal portion of the 40 kDa protein, was purified and cloned into the Sac I - Hind III digested pUC9-3. The resulting plasmid was designated pUC 9-1. This plasmid contained the entire coding sequence for the 40 kDa truncated PMSA fused to the leader and flanked by two Bam H1 sites. The 1.2 kb Bam Hl fragment from pUC 9-1 was purified and cloned into the Bam HI sites of pAc36C. The resulting plasmid was designated pAc36CP40pl.

Figure 6:
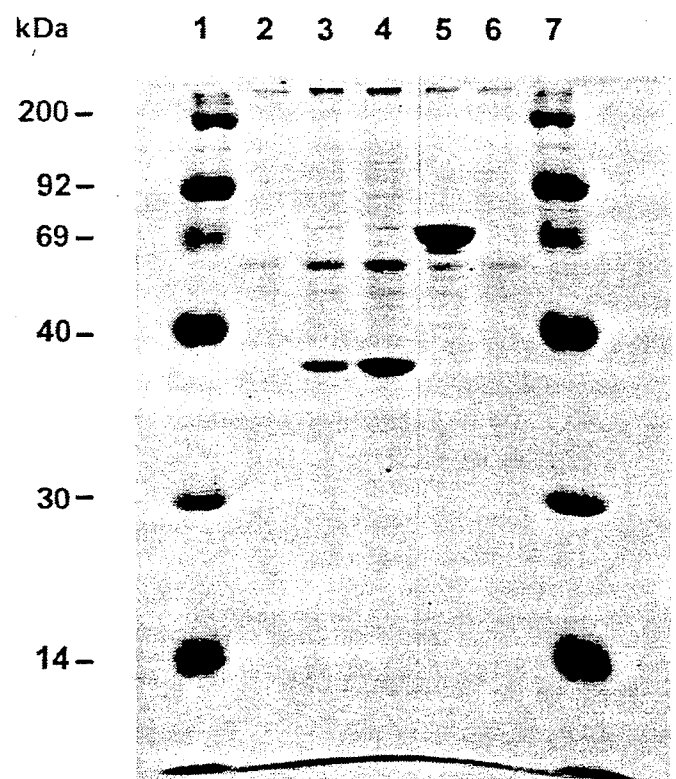
FIG. 6 shows the results of sodium dodecyl sulphate-polyacrylamide gel electrophoresis (SDS-PAGE) of cell infected with vP40, v36CP40pl and v36P60pl (lanes 3 to 5), whilst lanes 1 and 7 contain protein molecular weight markers and lanes 2 and 6: uninfected cells.

3. Generation of recombinant virus and analysis of proteins from cells infected with the recombinant viruses This was performed as described in Example 2. The resulting high titre viruses were called v36CP60pl, v36CP40 and v36CP40pl. Infected cells were lysed with 5% SDS and the products analysed by SDS/polyacrylamide electrophoresis on 10% gels followed by Coomassie blue staining. The results are shown in FIG. 6.

The identity and antigenicity of these products was confirmed by Western blotting using a polyclonal rabbit antisera (not shown). The 60 kDa product (lane 5) actually migrated as a 69 kDa band. The reason for this anomalous migration is unclear. The predicted molecular weight as determined from the amino acid sequence is 60 kDa. The 60 kDa product shows some breakdown to the 40 kDa product which cross-reacts with the antibody. Both the 40 kDa and 60 kDa proteins are stable as determined by pulse-chase experiments (data not shown). The levels of expression were as indicated above, demonstrating the superiority of the use of the leader sequence of the invention.

EXAMPLE 4

Expression of the human immunodeficiency virus (HIV) integrase protein

1. General

Two constructs were prepared and assayed. The first, v36HIVK, contained the integrase gene body fused to a perfect Kozak leader sequence. The second, v36HIVP, contained the integrase gene body fused to the leader sequence of the invention. The level of expression of the integrase protein by v36HIVP was 4-5 fold better than the level of expression of the integrase protein by v36HIVK.

2. Construction of plasmids pAc36CHIVK and pAc36-CHIVP

The fragment of DNA containing the integrase gene in pAc36CHIVK and pAc36CHIVP was derived from the plasmid pINpUC19. This construction contained the HIV integrase protein coding sequence on a 1.6 kbp Kpn I - Hind III fragment (Sherman and Fyfe, PNAS USA, 87, 5119-5123, 1990). A Nde I site had been introduced by site directed mutagenesis immediately adjacent to the N-terminal phenylalanine of the HIV integrase protein. Plasmids pAc36CHIVP and pAc36-CHIVK were constructed by purifying the 898bp Nde I fragment from pINpUC19 by gel electrophoresis followed by gel electroelution. The fragment was then ligated to one of the pairs of oligonucleotides shown in FIG. 7 and cloned into the Bam HI site of pAc36C. The construction containing the leader of the invention fused to the ATG was called pAc36HIVP (FIG. 7a) whilst that containing the perfect Kozak concensus sequence was called pAc36CHIKK.

Figure 8:
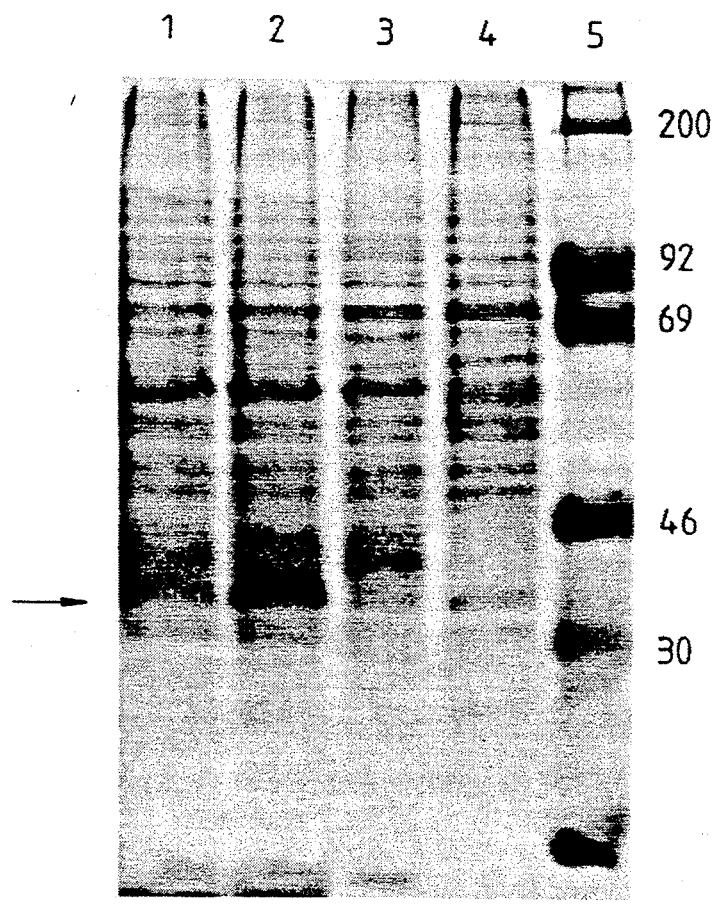
FIG. 8 shows SDS-PAGE analysis of lysates of insect cells expressing the integrase protein from HIV-1, in which Lane 1; Lysate of cells infected with vAc36-CHIV/K. Lane 2; Lysate of cells infected with vAc36-CHIV/P. lane 3; Lysate of cells infected with wild type virus. Lane 4; Lysate of uninfected cells. Lane 5; Protein molecular weight markers (The arrow indicates the HIV integrase band)

3. Generation of recombinant virus and analysis of proteins from cells infected with the recombinant viruses This was performed as described in Example 2. The resulting high titre viruses were called v36CIntK and v36CIntP. Infected cells ($2 \times 10^6$, 72 hpi) were lysed with 100 µl of 150 mM Tris, 5% SDS, 25% glycerol and 0.1% w/v bromophenol blue. Samples of these lysates were analysed on 10% SDS-PAGE gels (FIG. 8). Cells infected with vAc36C HIV/P expressed the HIV integrase protein at around 5 fold higher levels than cells infected with vAc36CHIV/K.

We claim:

1. A process for preparing a protein, which process comprises culturing, under such conditions that said protein is obtained, insect cells infected with a recombinant baculovirus having a promoter capable of directing expression of a heterologous gene having a coding sequence encoding said protein, said promoter being operably linked to said heterologous gene and said coding sequence being preceded by an untranslated leader of sequence T A A T C A T C C A C A G G A G A C T T T C T G (SEQ ID No: 1).

2. The process according to claim 1, wherein said leader is immediately preceded by the sequence A T C C.

3. The process according to claim 1, wherein said leader is fused to the translation initiation codon of said coding sequence.

4. The process according to claim 1, wherein said coding sequence encodes a protein selected from the group consisting of tetanus toxin fragment C, stromelysin, pertussis major surface antigen and human immunodeficiency virus integrase protein.

5. The process according to claim 1, wherein said promoter is the polyhedrin promoter.

6. The process according to claim 1, wherein said insect cells are cells of a *Spodoptera frugiperda* cell line.

7. The process according to claim 1, further comprising isolating and purifying said protein.

8. A recombinant baculovirus having a promoter capable of directing expression of a heterologous gene having a coding sequence in insect cells infected with said recombinant baculovirus, said promoter being operably linked to said heterologous gene, and said coding sequence being preceded by an untranslated leader of sequence T A A T C A T C C A C A G G A G A C T T T C T G (SEQ ID No: 1).

9. The recombinant baculovirus according to claim 8, wherein said leader is immediately preceded by the sequence A T C C.

10. The recombinant baculovirus according to claim 8, wherein said leader is fused to the translation initiation codon of said coding sequence.

11. The recombinant baculovirus according to claim 8, wherein said coding sequence encodes a protein selected from the group consisting of tetanus toxin fragment C, stromelysin, pertussis major surface antigen and human immunodeficiency virus integrase protein.

12. The recombinant baculovirus according to claim 8, wherein said promoter is the polyhedrin promoter.

13. A process for preparing a recombinant baculovirus, which process comprises:

(a) providing a recombinant baculovirus transfer vector having a promoter capable of directing expression of a heterologous gene in insect cells infected with a recombinant baculovirus, said promoter being operably linked to said heterologous gene, and said coding sequence being preceded by an untranslated leader of sequence
T A A T C A T C C A C A G G A G A C T T T C T G (SEQ ID No: 1); and (b) co-transfecting said cells with said vector and intact wild type baculovirus DNA.

14. The process according to claim 13, wherein said leader is immediately preceded by the sequence A T C C.

15. The process according to claim 13, wherein said leader is fused to the translation initiation codon of said coding sequence.

16. The process according to claim 13, wherein said coding sequence encodes a protein selected from the group consisting of tetanus toxin fragment C, stromelysin, pertussis major surface antigen and human immunodeficiency virus integrase protein.

17. The process according to claim 13, wherein said promoter is the polyhedrin promoter.

18. The process according to claim 13, wherein said insect cells are cells of a *Spodoptera frugiperda* cell line.

19. A recombinant baculovirus transfer vector for use in the preparation of a recombinant baculovirus, which vector has a promoter capable of directing expression of a heterologous gene having a coding sequence in insect cells infected with said recombinant baculovirus, said promoter being operably linked to said heterologous gene, and said coding sequence being preceded by an untranslated leader of sequence
T A A T C A T C C A C A G G A G A C T T T C T G (SEQ ID No: 1).

20. A baculovirus transfer vector comprising
(i) a restriction site into which a heterologous gene may be cloned downstream of the sequence encoding the N-terminus of polyhedrin;
(ii) another triplet of nucleotides in place of the natural ATG translation start condon of the polyhedrin coding sequence;
(iii) from up to the first 24 to up to the first 50 bases of the polyhedrin coding sequence; and
(iv) downstream of (iii) but upstream of (i), an untranslated leader of sequence
T A A T C A T C C A C A G G A G A C T T T C T G (SEQ ID NO: 1).

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

TAATCATCCA CAGGAGACTT TCTG        24

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

ATCCTAATCA TCCACAGGAG ACTTTCTG        28

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO (x i) SEQUENCE DESCRIPTION: SEQ ID NO:3:

AGCTTGGATC CTAATCATCC ACAGGAGACT TTCTG    35

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:4:

AGATCTTAAT CATCCACAGG AGACTTTCTG ATG    33

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:5:

GATCCGAATT CATGT    15

(2) INFORMATION FOR SEQ ID NO:6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:6:

GAATTCAATA TGG    13

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (i i) MOLECULE TYPE: DNA (genomic)

(i i i) HYPOTHETICAL: YES (i x) FEATURE:
        (A) NAME/KEY: miscfeature
        (B) LOCATION: complement (1..4)
        (D) OTHER INFORMATION: /function="Hind III 5'STICKY END"

(x i) SEQUENCE DESCRIPTION: SEQ ID NO:7:

AGCTTGGATC CGAATTCATG    20

( 2 ) INFORMATION FOR SEQ ID NO:8:

( i ) SEQUENCE CHARACTERISTICS:
        ( A ) LENGTH: 43 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: YES ( i v ) ANTI-SENSE: NO ( i x ) FEATURE:
        ( A ) NAME/KEY: miscfeature
        ( B ) LOCATION: complement (1..4)

( x i ) SEQUENCE DESCRIPTION: SEQ ID NO:8:

```
AGCTTGGATC CTAATCATCC ACAGGAGACT TTCTGAATTC ATG                    43
```

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

```
TTCTGAACAT CAGAAAGTCT                                              20
```

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:10:

```
GGATCCGAAT TCATG                                                   15
```

( 2 ) INFORMATION FOR SEQ ID NO:11:

( i ) SEQUENCE CHARACTERISTICS:
        ( A ) LENGTH: 11 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: miscfeature
        ( B ) LOCATION: complement (1..4)

( i x ) FEATURE:
        ( A ) NAME/KEY: miscfeature
        ( B ) LOCATION: complement (1..4)

-continued ( D ) OTHER INFORMATION: /function="Bam HI 5'STICKY END"

( x i ) SEQUENCE DESCRIPTION: SEQ ID NO:11:

GATCCAATAT G                                                                    1 1

( 2 ) INFORMATION FOR SEQ ID NO:12:

( i ) SEQUENCE CHARACTERISTICS:
                    ( A ) LENGTH: 32 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

GATCCTAATC ATCCACAGGA GACTTTCTGA TG                                             3 2

( 2 ) INFORMATION FOR SEQ ID NO:13:

( i ) SEQUENCE CHARACTERISTICS:
                    ( A ) LENGTH: 32 base pairs
                    ( B ) TYPE: nucleic acid
                    ( C ) STRANDEDNESS: both
                    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
                    ( A ) NAME/KEY: miscfeature
                    ( B ) LOCATION: complement (1..4)
                    ( D ) OTHER INFORMATION: /function="Bam HI 5'STICKY END"

( x i ) SEQUENCE DESCRIPTION: SEQ ID NO:13:

GATCCTAATC ATCCACAGGA GACTTTCTTA TG                                             3 2

( 2 ) INFORMATION FOR SEQ ID NO:14:

( i ) SEQUENCE CHARACTERISTICS:
                    ( A ) LENGTH: 18 base pairs
                    ( B ) TYPE: nucleic acid
                    ( C ) STRANDEDNESS: both
                    ( D ) TOPOLOGY: linear ( i i ) MOLECULE TYPE: DNA (genomic)

( i i i ) HYPOTHETICAL: NO ( i x ) FEATURE:
                    ( A ) NAME/KEY: miscfeature
                    ( B ) LOCATION: complement (1..4)
                    ( D ) OTHER INFORMATION: /function="Bam HI 5'STICKY END"

( x i ) SEQUENCE DESCRIPTION: SEQ ID NO:14:

GATCCCGCCG CCACTATG                                                             1 8

( 2 ) INFORMATION FOR SEQ ID NO:15:

( i ) SEQUENCE CHARACTERISTICS:
                    ( A ) LENGTH: 1160 base pairs
                    ( B ) TYPE: nucleic acid
                    ( C ) STRANDEDNESS: both
                    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

| | | | | | | |
|---|---|---|---|---|---|---|
| GAATTCATGT | TCAGAACCTT | TCCTGGCATC | CCGAAGTGGA | GGAAAACCCA | CCTTACATAC | 60 |
| AGGATTGTGA | ATTATACACC | AGATTTGCCA | AAAGATGCTG | TTGATTCTGC | TGTTGAGAAA | 120 |
| GCTCTGAAAG | TCTGGGAAGA | GGTGACTCCA | CTCACATTCT | CCAGGCTGTA | TGAAGGAGAG | 180 |
| GCTGATATAA | TGATCTCTTT | TGCAGTTAGA | GAACATGGAG | ACTTTTACCC | TTTTGATGGA | 240 |
| CCTGGAAATG | TTTTGGCCCA | TGCCTATGCC | CCTGGGCCAG | GGATTAATGG | AGATGCCCAC | 300 |
| TTTGATGATG | ATGAACAATG | GACAAAGGAT | ACAACAGGGA | CCAATTTATT | TCTCGTTGCT | 360 |
| GCTCATGAAA | TTGGCCACTC | CCTGGGTCTC | TTTCACTCAG | CCAACACTGA | AGCTTTGATG | 420 |
| TACCCACTCT | ATCACTCACT | CACAGACCTG | ACTCGGTTCC | GCCTGTCTCA | AGATGATATA | 480 |
| AATGGCATTC | AGTCCCTCTA | TGGACCTCCC | CCTGACTCCC | CTGAGACCCC | CCTGGTACCC | 540 |
| ACGGAACCTG | TCCCTCCAGA | ACCTGGGACG | CCAGCCAACT | GTGATCCTGC | TTTGTCCTTT | 600 |
| GATGCTGTCA | GCACTCTGAG | GGGAGAAATC | CTGATCTTTA | AAGACAGGCA | CTTTTGGCGC | 660 |
| AAATCCCTCA | GGAAGCTTGA | ACCTGAATTG | CATTTGATCT | CTTCATTTTG | GCCATCTCTT | 720 |
| CCTTCAGGCG | TGGATGCCGC | ATATGAAGTT | ACTAGCAAGG | ACCTCGTTTT | CATTTTTAAA | 780 |
| GGAAATCAAT | TCTGGGCCAT | CAGAGGAAAT | GAGGTACGAG | CTGGATACCC | AAGAGGCATC | 840 |
| CACACCCTAG | GTTTCCCTCC | AACCGTGAGG | AAAATCGATG | CAGCCATTTC | TGATAAGGAA | 900 |
| AAGAACAAAA | CATATTTCTT | TGTAGAGGAC | AAATACTGGA | GATTTGATGA | GAAGAGAAAT | 960 |
| TCCATGGAGC | CAGGCTTTCC | CAAGCAAATA | GCTGAAGACT | TTCCAGGGAT | TGACTCAAAG | 1020 |
| ATTGATGCTG | TTTTTGAAGA | ATTTGGGTTC | TTTTATTTCT | TTACTGGATC | TTCACAGTTG | 1080 |
| GAGTTTGACC | CAAATGCAAA | GAAAGTGACA | CACACTTTGA | AGAGTAACAG | CTGGCTTAAT | 1140 |
| TGTTGATAAC | TGCAGGATCC | | | | | 1160 |